United States Patent
Amann et al.

[11] Patent Number: 6,066,155
[45] Date of Patent: *May 23, 2000

[54] CAPTURED SLEEVE AND STENT DELIVERY DEVICE

[75] Inventors: Rainer Amann, Klettgau/Riedern a.S., Germany; Erwin Berger, Mattwil, Switzerland

[73] Assignee: Schneider (Europe) A.G., Bulach, Switzerland

[ * ] Notice: This patent is subject to a terminal disclaimer.

[21] Appl. No.: 08/933,220

[22] Filed: Sep. 18, 1997

[30] Foreign Application Priority Data

Nov. 15, 1996 [EP] European Pat. Off. .............. 96203188

[51] Int. Cl.[7] ....................................................... A61M 5/32
[52] U.S. Cl. .......................... 606/192; 604/104; 604/527; 604/536
[58] Field of Search .............................. 604/96, 104, 163, 604/263, 264, 912, 915, 917, 523, 525, 526, 527, 535, 536; 606/191, 192, 194

[56] References Cited

U.S. PATENT DOCUMENTS

| | | | |
|---|---|---|---|
| 4,921,479 | 5/1990 | Grayzel | 604/53 |
| 5,049,131 | 9/1991 | Deuss | 604/96 |
| 5,201,757 | 4/1993 | Heyn et al. | |
| 5,242,399 | 9/1993 | Lau et al. | 604/104 |
| 5,246,421 | 9/1993 | Saab | |
| 5,312,356 | 5/1994 | Engelson et al. | 604/164 |
| 5,437,650 | 8/1995 | Larkin et al. | 604/283 |
| 5,509,911 | 4/1996 | Cottone, Sr. et al. | 604/283 |
| 5,549,551 | 8/1996 | Peacock, III et al. | 604/96 |
| 5,662,700 | 9/1997 | Lazarus | 623/1 |
| 5,676,654 | 10/1997 | Ellis et al. | 604/103 |
| 5,735,869 | 4/1998 | Fernandez-Aceytuno | 606/194 |
| 5,782,854 | 7/1998 | Hermann | 606/194 |
| 5,843,092 | 12/1998 | Heller et al. | 606/108 |
| 5,891,154 | 4/1999 | Loeffler | 606/108 |

FOREIGN PATENT DOCUMENTS

| | | |
|---|---|---|
| 0408245A1 | 1/1991 | European Pat. Off. . |
| 0466518A2 | 1/1992 | European Pat. Off. . |
| 0727194A1 | 8/1996 | European Pat. Off. . |
| 95/08965 | 4/1995 | WIPO . |

*Primary Examiner*—Ronald Stright
*Assistant Examiner*—Jeremy Thissell
*Attorney, Agent, or Firm*—Vidas, Arrett & Steinkraus P.A.

[57] ABSTRACT

A balloon catheter with a tubular catheter shaft having a proximal and a distal end. The elongated dilatation balloon is arranged on the catheter shaft in the vicinity of the distal end. An indispensable covering sleeve is movable along the catheter shaft. The covering sleeve has a first portion with a first inner diameter surrounding the catheter shaft and a second portion with a second inner diameter being pushable over the deflated dilatation balloon. The second inner diameter is larger than said first inner diameter. The covering sleeve provides continuous adjustability of the fuller expandable balloon length.

15 Claims, 5 Drawing Sheets

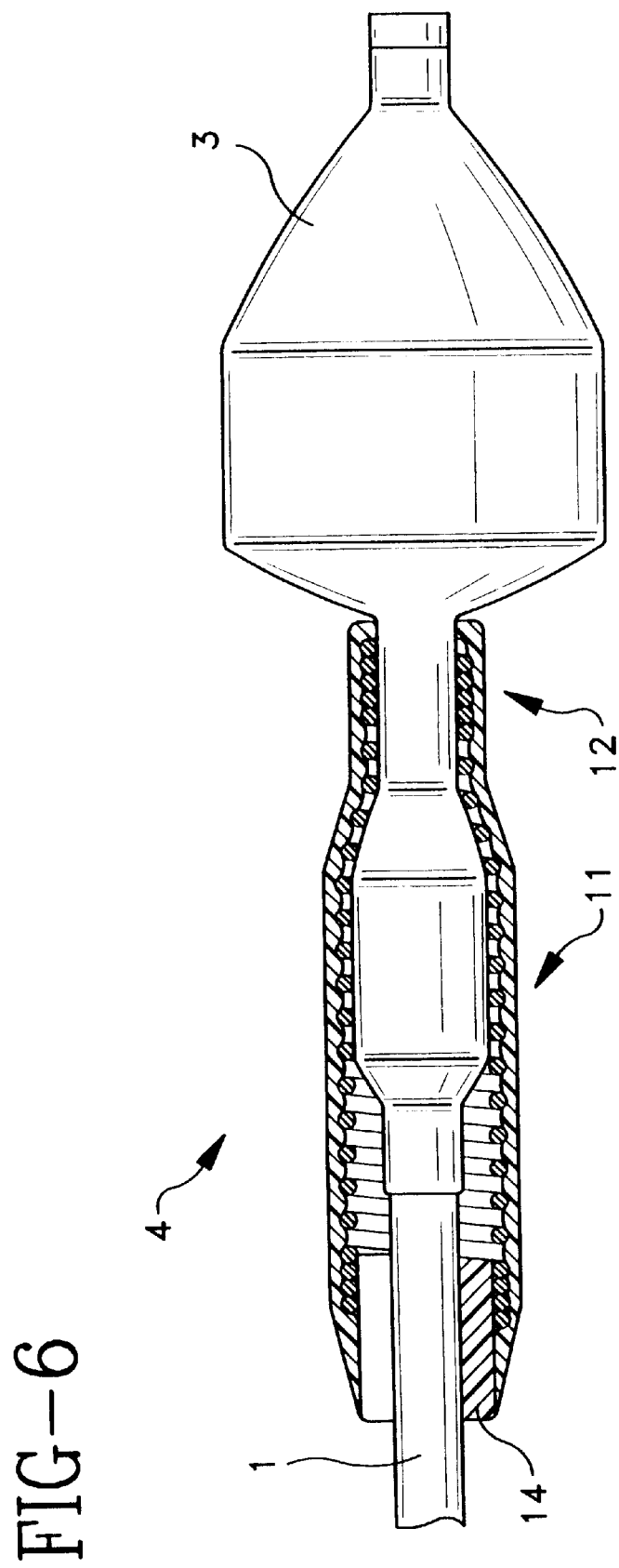

CAPTURED SLEEVE AND STENT DELIVERY DEVICE

BACKGROUND OF THE INVENTION

The invention relates to a balloon catheter with an indispensable covering sleeve being movable along the catheter shaft. The invention also relates to a delivery device for a balloon-expandable stent.

In the balloon catheter technology, it is known to use balloon catheters with fixed balloon lengths. Many medical procedures require the application of several balloon catheters with different balloon lengths. If an intervention demands, for instance, two differently long balloons, it is necessary to change the balloon catheter or to use the same balloon sequentially. The change of a balloon catheter is, however, very costly while sequential action is time consuming. Moreover, the risk of injury for the patient is increased or insufficient dilatations might be achieved.

A balloon catheter is also an instrument of common use for the transport and expansion of a balloon-expandable prosthesis such as a stent, which is implanted for maintaining the patency of a vessel. Here, the length of the balloon has to be chosen in dependence on the length of the stent in order to avoid inappropriate expansion of the stent or damage to the vessel. This inevitably leads to the costly need of a plurality of balloon catheters with different balloon lengths to correctly and safely apply stents.

The document EP 0 727 194 A1 shows a balloon catheter in which an indispensable covering sleeve can take two different positions. In its proximal end position, the covering sleeve uncovers the full balloon length for expansion, while in its distal end position, it covers a proximal portion of the balloon and prevents this from an expansion to the nominal balloon diameter. With such a balloon catheter, a selection can be made between two different balloon lengths. The distal end position is secured by friction fit upon pushing the covering sleeve onto an enlarged portion of the catheter shaft. The covering sleeve also comprises a tampered distal end without armature means which in use, however, is expanded by the pressurized dilatation balloon. The fully expanded part of the dilatation balloon then applied a proximal directed force against the covering sleeve which might cause it to migrate. Intermediate positions of the covering sleeve and consequently intermediate values of the balloon length cannot be selected with this catheter. In such a case, the position of the covering sleeve would not be secured and could migrate under the dilation pressure.

All documents cited herein, including the foregoing, are incorporated herein by reference in their entireties for all purposes.

SUMMARY OF THE INVENTION

Accordingly, the invention relates to a balloon catheter with a tubular catheter shaft having a proximal and a distal end, an elongated dilatation balloon being arranged on the catheter shaft in the vicinity of the distal end thereof, and an indispensable covering sleeve being movable along the catheter shaft. The covering sleeve has a first portion with a first inner diameter surrounding the catheter shaft and a second portion with a second inner diameter being pushable over the deflated dilatation balloon. The second inner diameter is larger than said first inner diameter. The invention also relates to a delivery device for a balloon-expandable stent.

The balloon catheter has a balloon length which is continuously selectable and the selected balloon length is secured upon inflation of the dilatation balloon. Moreover, a delivery device for balloon-expandable stents of different lengths is provided which is versatile as well as simple and safe in its handling.

When the covering sleeve comprises at the outside end of the second portion and indispensable third portion having a third inner diameter which is larger than the first inner diameter and smaller than the second inner diameter, during inflation of the dilatation balloon, the third portion is stable confined between the partly expandable balloon portion being covered by the second portion and the free fully expandable balloon portion. In this state, the axial position of the covering sleeve is held by the dilatation pressure so that a continuous adjustability of the balloon length is achieved without extra safety means based on friction fit. In practical use, be it for the dilatation of stenosis or for stent delivery, a balloon catheter according to the invention can be performed as an over-the-wire catheter as well as a MONO-RAIL® catheter. In both cases, it is possible to push the covering sleeve either from the proximal or the distal end onto the deflated dilatation balloon and so to continuously adjust the freely expandable balloon length.

In a preferred embodiment of the invention, the covering sleeve is movable onto the deflated dilatation balloon from the proximal end whereby the first portion is arranged proximal and the third portion is arranged distal from the second portion of the covering sleeve. In this case, the covering sleeve does not have to be pushed through the lesion during introduction of the balloon catheter into a blood vessel, but after positioning of the dilatation balloon it takes a position proximal of the stenosis.

In an advantageous embodiment of the invention, the second portion of the covering sleeve and one of the outside portions are formed integral in one piece and the other outside portion is inserted in the second portion which facilitates the manufacturing process.

Portions of the covering sleeve which are formed integral in one piece preferably comprise an indispensable flexible armature to withstand the high inflation pressures of the dilatation balloon and adapt to narrow vessel curvatures while the balloon catheter is advanced in a vessel system.

In a further preferred embodiment of the invention, the inserted portion of the covering sleeve is formed by a tension element closely surrounding the catheter shaft. The friction fit between the tension element and the catheter shaft caused by the tensioning force fixes a pre-adjusted axial position of the covering sleeve on the catheter shaft. Thereby, it reduces the chance that an adjusted balloon length will be displaced during introduction of the balloon catheter into the body of a patient. The tension element is preferably a longitudinally slotted tension husk, since such a part is especially easy to produce. The slit guarantees a tight placement of the tension husk even with small manufacturing tolerances.

In another advantageous embodiment of the invention, the covering sleeve comprises a jacket covering the armature and the tension element. It imparts a smooth atraumatic outer surface to the covering sleeve whereby the good guiding properties of the balloon catheter are conserved and the risk of injury for the patient is reduced.

The catheter shaft comprises a proximal and a distal stop between which the covering sleeve is movable along the catheter shaft. This secures the covering sleeve against loss from he catheter shaft. The proximal stop is preferably a shoulder on the catheter shaft and the distal stop is preferably formed by the proximal fixture of the dilatation balloon on the catheter shaft or by the folded deflated dilatation balloon itself. In the latter case, no special extra measures for the distal stop are required. The stops represent portions of the catheter shaft which are enlarged in diameter and cannot be passed by the covering sleeve due to the tension elements which are tightly enclosing the catheter shaft.

The armature can be made of a helically wound wire material or formed by a tubular wire braiding. Both embodiments generally have high flexibility and are generally pressure resistant regarding the stability of diameter. When the armature is made of a raidiopaque material, the covering sleeve can be visualized during the intervention on an X-ray screen.

With the balloon catheter as described above, the essential element of a delivery device for balloon-expandable stent of different lengths is created. The advantage of a device according to the invention lies especially in the fact that, for example, it can be used initially for pre-dilatation of a stenosis with a first balloon length and afterwards for the deployment of a stent with a second balloon length by retracting the device after dilatation of the stenosis from the vessel along the guidewire, then followed by adjusting the new balloon length by means of the covering sleeve, and mounting the stent to be implanted in its unexpanded state onto the freely expandable balloon portion. Afterwards, the balloon catheter is again advanced to the pre-dilated vessel site to transfer the stent into its expanded state by another inflation of the dilatation balloon. If necessary, post-dilatation of the stent can still be performed with the same balloon catheter and perhaps with a third balloon length.

In sum, the invention relates to a balloon catheter including a tubular catheter shaft having a proximal and a distal end, and elongated dilation balloon arranged on the catheter shaft in the vicinity of the distal end, and an indispensable covering sleeve which is movable along the catheter shaft. The covering sleeve has a first portion with a first inner diameter surrounding the catheter shaft and a second portion with a second inner diameter being movable over the deflated dilatation balloon. The second inner diameter is larger than the first inner diameter and the covering sleeve includes an indispensable third portion with a third inner diameter at the outside end of the second portion. The third inner diameter is between from about the first inner diameter to about the second inner diameter. The covering sleeve may be movable from proximal end onto the deflated dilatation balloon and the first portion is arranged proximally and the third portion is arranged distally of the second portion of the covering sleeve. The second portion of the covering sleeve and one of the outside portions may be formed integral in one piece and the other of the outside portion is inserted in the second portion. The portions of the covering sleeve may be formed integral in one piece and have an indispensable flexible armature. The inserted portions of the covering sleeve may be formed by a tensioning element closely surrounding the catheter shaft. The tensioning element may be a longitudinally slotted tensioning husk. The covering sleeve may include a jacket covering a armature and the tensioning element. The catheter shaft may include a proximal stop and a distal stop, and the covering sleeve may be movable along the catheter shaft between the stops. The proximal stop may be a shoulder on the catheter shaft. The distal stop may be formed by a proximal fixture of the dilatation balloon on the catheter shaft. The distal stop may be formed by a folded deflated dilatation balloon. The armature may be made of a helically wound wire material. The armature may be formed by a tubular wire braiding. The armature may be made of a radiopaque material. The balloon catheter may further include a balloon expandable stent disposed on a portion of the balloon and the balloon catheter is adapted to be used as a delivery device for the balloon expandable stent.

Self-expanding medical prostheses frequently referred to as stents are well known and commercially available. They are, for example, disclosed generally in the Wallsten U.S. Pat. No. 4,655,771 and the Wallsten et al. U.S. Pat. No. 5,061,275.

Still other objects and advantages of the present invention and methods of construction of the same will become readily apparent to those skilled in the are from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

FIG. 6 shows the arrangement from FIG. 3 in magnification whereby the covering sleeve is depicted in longitudinal section.

DETAILED DESCRIPTION OF THE INVENTION

Figure 1:
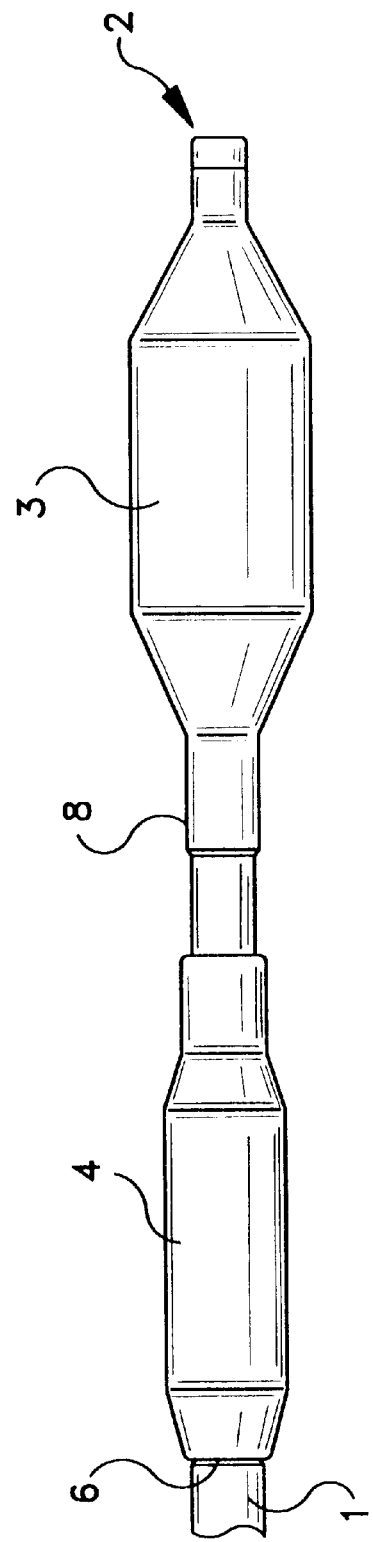
FIG. 1 is a side elevation of the balloon catheter whereby the covering sleeve is moved into its proximal end position.
Figure 2:
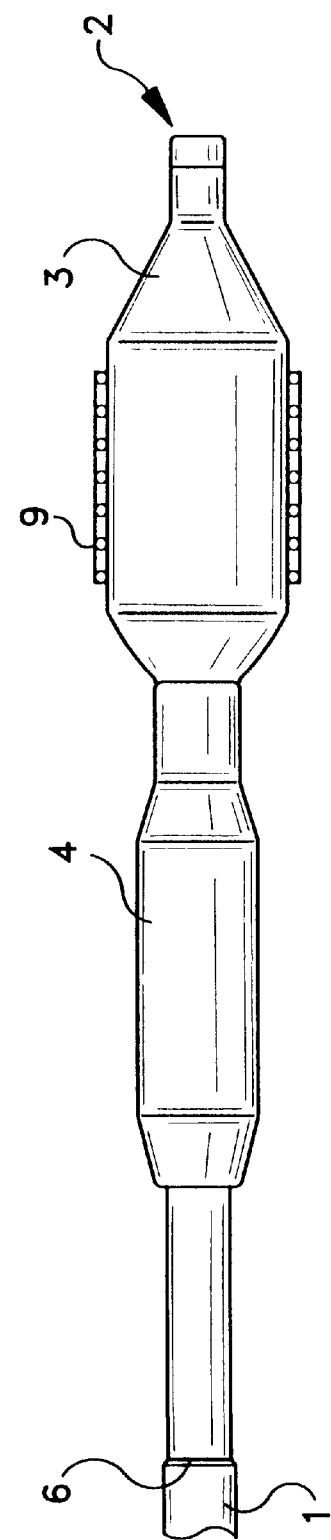
FIG. 2 is a side elevation of a stent delivery device for balloon-expandable stents whereby the covering sleeve of the balloon catheter partly covers the dilatation balloon.
Figure 3:
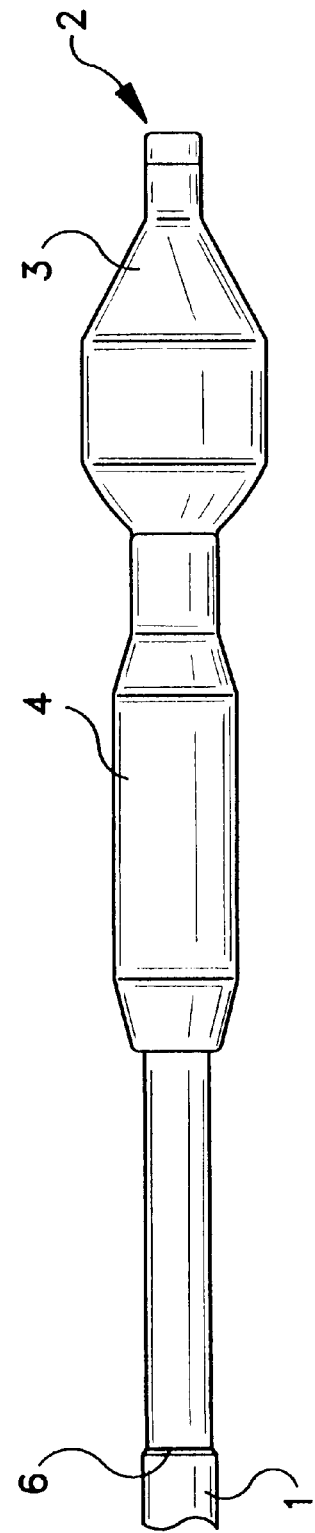
FIG. 3 is a side elevation of the balloon catheter whereby the covering sleeve is moved into a distal position.

FIGS. 1–3 show a balloon catheter according to the invention with a tubular catheter shaft 1 comprising a proximal end (not shown) and a distal end 2 at which an elongated dilatation balloon 3 is arranged. Proximal of the dilatation balloon 3, the balloon catheter comprises an indispensable covering sleeve 4 which is continuously movable along the catheter shaft 1 between a proximal stop which, in this embodiment, is a shoulder 6 and a distal stop which, in this case, is formed by the proximal fixture 8 of the dilatation balloon 3 on the catheter shaft 1. The distal stop can also be the folded deflated dilatation balloon 3. In FIG. 1, the covering sleeve 4 is shown in its proximal end position where the entire balloon length can be used for dilatation. In the stent delivery device for balloon-expandable stents 9 as shown in FIG. 2, the covering sleeve 4 is pushed partially over the deflated dilatation balloon 3 for shortening of the fully expandable balloon length in order to adapt the balloon length to the length of the stent 9. To adjust to an especially short balloon length, the covering sleeve 4 can be moved close to its distal end position is shown in FIG. 3. Depending on the practical requirements, further balloon lengths which are not shown in the figures can be achieved by shifting the covering sleeve 4 respectively.

Figure 4:
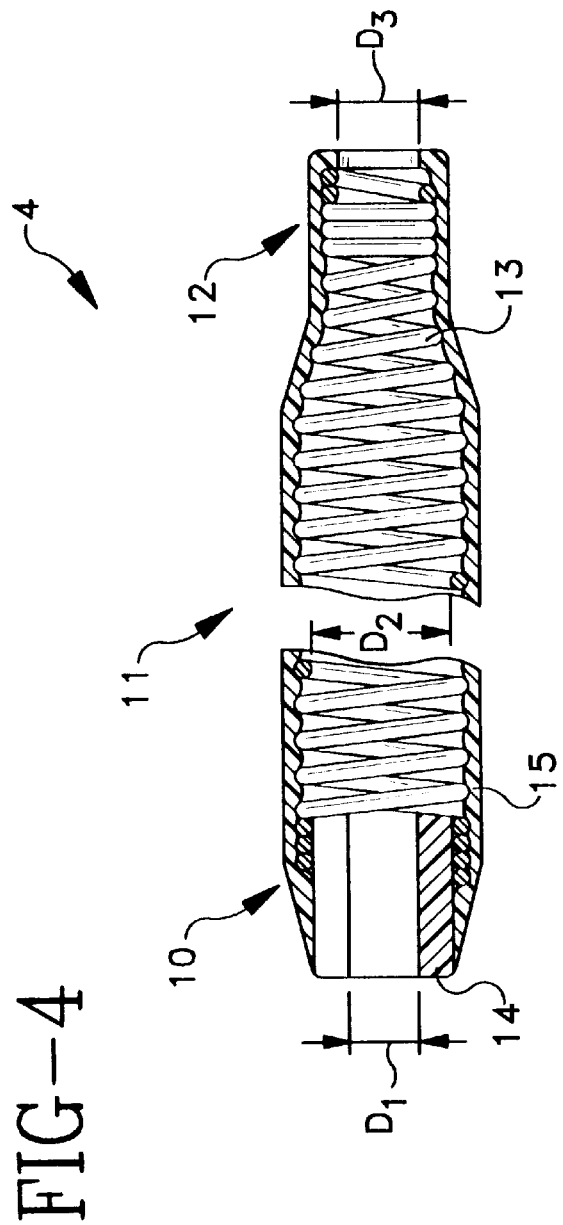
FIG. 4 is a longitudinal section of the covering sleeve of the balloon catheter.
Figure 5:
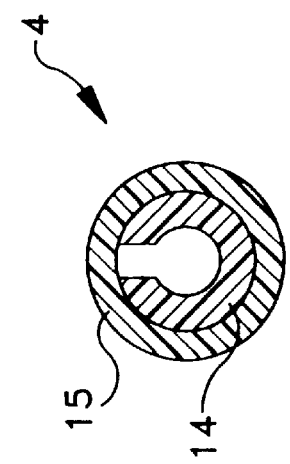
FIG. 5 is a cross section in the region of the tension husk.

According to FIG. 4, the covering sleeve 4 comprises proximally a first portion 10 with a first inner diameter $D_1$ followed by a second portion 11 with a second inner diameter $D_2$ which is larger than the first inner diameter $D_1$. Distally of the second portion 11, the covering sleeve 4 comprises an indispensable third portion 12 with a third inner diameter $D_3$ which ranges from the first inner diameter $D_1$ to the second inner diameter $D_2$. For reasons of clarity, the covering sleeve 4 is not shown in its real length; at a total length of the covering sleeve 4 of about 20 mm, the third portion 12 is only about 1 mm long. The second portion 11 and the third portion 12 are formed integral in one piece with an armature 13 which is stable in diameter and made of a helically wound wire material in order to withstand the dilatation pressure of the covered balloon portion. The first portion 10 is formed by a tensioning element 14 and is inserted in the second portion 11. Alternatively, all portions 10, 11 and 12 of the covering sleeve 4 can be formed integral in one piece whereby the armature is, for instance, a continuous wire coil. The armature 13 and tension element 14 are enclosed by a jacket 15 in order to impart a smooth a traumatic outer surface to the covering sleeve 4. The structure of the inner surface of the jacket 15 represents an embedding for the armature 13 while the tension element 14 is distally surrounded by windings of the armature 13 and proximally glued directly into the jacket 15. FIG. 5 shows a cross section of the covering sleeve 4 in the region of this glue joint. The tension element 14 is formed by a longitudinally slotted tensioning husk and is enclosed by the jacket 15. The slot serves as a compensation for tolerances in the diameter of the catheter shaft 1. The slot in the tension husk can be omitted if the catheter shaft 1 is manufactured sufficiently exact.

According to FIG. 6, the tensioning element 14 surrounds the catheter shaft 1 proximally of the dilatation balloon 3 so tightly that a sufficiently strong friction fit between the tension husk and the catheter shaft 1 provides for a safe axial positioning of the covering sleeve 4. The second portion 11 and the third portion 12 are moved over the dilatation balloon 3 in such a way that upon inflation of the dilatation balloon 3, the indispensable third portion 12 is confined proximally by the partially expanded covered portion and distally by the fully expanded free portion of the dilatation balloon 3. This guarantees a continuously variable balloon length which is fixedly secured during application of the balloon catheter once it is pre-selected.

It will be evident from considerations of the foregoing that the Captured Sleeve and Stent Delivery Device is now available, and may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A balloon catheter comprising:
    a tubular catheter shaft having a proximal and a distal end, an elongated dilatation balloon being arranged on the catheter shaft in the vicinity of the distal end thereof, and an indispensable covering sleeve being movable along the catheter shaft, the covering sleeve having a first portion with a first inner diameter surrounding the catheter shaft and a second portion with a second inner diameter being movable over the deflated dilatation balloon, the second inner diameter being larger than the first inner diameter wherein the covering sleeve comprises an indispensable third portion with a third inner diameter at the outside end of the second portion, the third inner diameter being less than the second inner diameter, and wherein the second an third portions are formed with an armature.

2. The balloon catheter according to claim 1 wherein the covering sleeve is movable from the proximal end onto the deflated dilatation balloon whereby the first portion is arranged proximally and the third portion is arranged distally of the second portion of the covering sleeve.

3. A balloon catheter comprising:
    a tubular catheter shaft having a proximal and a distal end, an elongated dilatation balloon being arranged on the catheter shaft in the vicinity of the distal end thereof, and an indispensable covering sleeve being movable along the catheter shaft, the covering sleeve having a first portion with a first inner diameter surrounding the catheter shaft and a second portion with a second dinner diameter being movable over the deflated dilatation balloon, the second inner diameter being larger than the first inner diameter wherein the covering sleeve comprises an indispensable third portion with a third inner diameter at the outside end of the second portion, the third inner diameter between from about the first inner diameter to about the second inner diameter, wherein the second portion of the covering sleeve and one of the first or third portions are formed integral in one piece and the other of the first or third portions is inserted in the second portion.

4. The balloon catheter according to claim 3 wherein portions of the covering sleeve are formed integral in one piece and have an indispensable flexible armature.

5. The balloon catheter according to claim 3 wherein the inserted portion of the covering sleeve consists of a tensioning element closely surrounding the catheter shaft.

6. The balloon catheter according to claim 5 wherein the tensioning element is a longitudinally slotted tensioning husk.

7. The balloon catheter according to claim 5 wherein the covering sleeve comprises a jacket covering the armature and the tensioning element.

8. The balloon catheter according to claim 2 wherein the catheter shaft comprises a proximal stop and a distal stop, and the covering sleeve is movable along the catheter shaft between the stops.

9. The balloon catheter according to claim 8 wherein the proximal stop is a shoulder on the catheter shaft.

10. The balloon catheter according to claim 8 wherein the distal stop is formed by a proximal fixture of the dilatation balloon on the catheter shaft.

11. The balloon catheter according to claim 9 wherein the distal stop is formed by a folded deflated dilatation balloon.

12. The balloon catheter according to claim 4 wherein the armature is made of a helically wound wire material.

13. The balloon catheter according to claim 4 wherein the armature is formed by a tubular wire braiding.

14. The balloon catheter according to claim 4 wherein the armature is made of a radiopaque material.

15. The balloon catheter according to claim 1 wherein the balloon catheter further comprises a balloon expandable stent disposed on a portion of the balloon.

* * * * *

UNITED STATES PATENT AND TRADEMARK OFFICE
CERTIFICATE OF CORRECTION

PATENT NO. : 6,066,155

DATED : May 23, 2000

INVENTOR(S) : RAINER AMANN

It is certified that error appears in the above-identified patent and that said Letters Patent is hereby corrected as shown below:

Col. 1, line 42, delete "applied" and insert -- applies --;
Col. 2, line 6, delete "and" and insert -- an --;
Col. 2, line 64, delete "he" and insert -- the --;
Col. 3, line 14, delete "stent" and insert -- stents --;
Col. 3, line 32, delete "and" and insert -- an --;
Col. 4, line 11, delete "are" and insert -- art --;
Col. 6, line 6, delete "an" and insert -- and --.

Signed and Sealed this

Twenty-seventh Day of March, 2001

Attest:

NICHOLAS P. GODICI

Attesting Officer

Acting Director of the United States Patent and Trademark Office